(12) United States Patent
Mostowfi et al.

(10) Patent No.: US 8,269,961 B2
(45) Date of Patent: Sep. 18, 2012

(54) SYSTEM AND METHOD FOR DETERMINING THE ASPHALTENE CONTENT OF CRUDE OIL

(75) Inventors: Farshid Mostowfi, Edmonton (CA); Abdel M. Kharrat, Edmonton (CA); Kentaro Indo, Edmonton (CA)

(73) Assignee: Schlumberger Technology Corporation, Sugar Land, TX (US)

( * ) Notice: Subject to any disclaimer, the term of this patent is extended or adjusted under 35 U.S.C. 154(b) by 358 days.

(21) Appl. No.: 12/790,927

(22) Filed: May 31, 2010

(65) Prior Publication Data

US 2011/0292382 A1    Dec. 1, 2011

(51) Int. Cl.
*G01N 1/10* (2006.01)
*G01J 3/28* (2006.01)

(52) U.S. Cl. .................. 356/246; 356/303; 356/326

(58) Field of Classification Search ............ 356/246, 356/300, 303, 319, 326, 451
See application file for complete search history.

(56) References Cited

U.S. PATENT DOCUMENTS

| | | | |
|---|---|---|---|
| 4,843,247 A | 6/1989 | Yamazoe et al. | |
| 4,950,610 A * | 8/1990 | Tittle | 436/163 |
| 5,266,800 A | 11/1993 | Mullins | |
| 5,572,320 A * | 11/1996 | Reintjes et al. | 356/335 |
| 6,992,768 B2 | 1/2006 | Dong et al. | |
| 7,088,446 B2 * | 8/2006 | Cerni | 356/335 |
| 7,736,900 B2 * | 6/2010 | Pauli et al. | 436/29 |
| 2004/0058451 A1* | 3/2004 | Pauli et al. | 436/163 |
| 2005/0146717 A1* | 7/2005 | Cerni | 356/326 |
| 2010/0251935 A1* | 10/2010 | Pauli et al. | 106/273.1 |

FOREIGN PATENT DOCUMENTS

WO    2009001096 A1    12/2008

OTHER PUBLICATIONS

Bouquet, M and Hamon, J, "Determination of Asphaltene Content in Petroleum Products for Concentrations Below 20000 ppm Down to 150 ppm", Fuel 1985, vol. 64, November, Butterworth & Co. Publishers Ltd. pp. 1625-1627.

Bowden S A et al: "Determination of the asphaltene and carboxylic acid content of a heavy oil using a microfluidic device"—Lab on a Chip Royal Society of Chemistry, UK—vol. 9, No. 6, Mar. 21, 2009, pp. 828-832, XP000002658276.

Rogel E. et al: "Determination of asphaltene in crude oil and petroleum products by the on column precipitation method"—Energy and Fuels 20090917 American Chemical Society, USA. vol. 23, No. 9, Sep. 17, 2009, pp. 4515-4521, XP000002658277.

Aske N et al: "Asphaltene Aggregation from crude oils and model systems studied by high-pressure NIR spectroscopy" Energy & Fuels, American Chemical Society, Washington DC, US. vol. 16, Aug. 9, 2002 pp. 1287-1295, XP001152465.

117.0060PCT—PCT/IB2011/051915—International Search Report dated Oct. 6, 2011.

\* cited by examiner

*Primary Examiner* — Roy M Punnoose
(74) *Attorney, Agent, or Firm* — Daren C. Davis; Wayne I. Kanak

(57) ABSTRACT

A system for determining the asphaltene content of crude oil includes a first optical flow cell, a first spectrometer operably associated with the first optical flow cell, and a mixer in fluid communication with the first optical flow cell. The system further includes a crude oil injection/metering device configured to receive the crude oil, the crude oil injection/metering device being in fluid communication with the first optical flow cell; a titrant injection/metering device in fluid communication with the mixer, the titrant injection/metering device configured to receive a titrant; and a filtration unit in fluid communication with the mixer. The system further includes a second optical flow cell in fluid communication with the filtration unit, and a second spectrometer operably associated with the second optical flow cell.

34 Claims, 7 Drawing Sheets

SYSTEM AND METHOD FOR DETERMINING THE ASPHALTENE CONTENT OF CRUDE OIL

BACKGROUND OF THE INVENTION

1. Field of the Invention

The present invention relates to a system and method for determining the asphaltene content of crude oil.

2. Description of Related Art

Asphaltenes are a solubility class of components of crude oil. Commonly, asphaltenes are defined as such components that are insoluble in pentane or heptane but that are soluble in toluene or dichloromethane. Asphaltenes are of particular interest to the petroleum industry because of their depositional effect in production equipment, such as in tubular members in oil wells. Additives are sometimes used to inhibit these deleterious effects. In addition, asphaltenes impart high viscosity to crude oils, negatively impacting production. The variable asphaltene concentration in crude oils within individual reservoirs can create a myriad of production problems. Accordingly, it is often desirable to determine the amount of asphaltenes in crude oil and a variety of methods exist for making such determinations.

Conventional methods for determining the asphaltene content of crude oil rely upon precipitating by a titrant and filtering the asphaltenes from the crude oil, then weighing the asphaltenes. Methods such as this, however, (1) are often not sufficiently repeatable and reproducible; (2) are well-suited for laboratory operations only; (3) require significant time to complete, often as long as two days or more; (4) require large volumes of samples that are inherently hazardous in nature; (5) are dependent upon controlled humidity environments for reliable results; and (6) are dependent upon operator skill for reliable results.

Although there are methods for determining the asphaltene content of crude oil that are well known in the art, considerable shortcomings remain.

BRIEF SUMMARY OF THE INVENTION

In one aspect, the present invention provides a system for determining the asphaltene content of crude oil. The system comprises a first optical flow cell, a first spectrometer operably associated with the first optical flow cell, and a mixer in fluid communication with the first optical flow cell. The system further comprises a crude oil injection/metering device configured to receive the crude oil, the crude oil injection/metering device being in fluid communication with the first optical flow cell; a titrant injection/metering device in fluid communication with the mixer, the titrant injection/metering device configured to receive a titrant; and a filtration unit in fluid communication with the mixer. The system further comprises a second optical flow cell in fluid communication with the filtration unit and a second spectrometer operably associated with the second optical flow cell.

In another aspect, the present invention provides a system for determining the asphaltene content of crude oil. The system comprises an injection/metering device configured to receive the crude oil and a titrant, a mixer in fluid communication with the injection/metering device, and a filtration unit in fluid communication with the mixer. The system further comprises an optical flow cell in fluid communication with the filtration unit and a spectrometer operably associated with the optical flow cell.

In yet another aspect, the present invention provides a method for determining the asphaltene content of crude oil. The method comprises obtaining a crude oil sample, determining an optical spectrum of the crude oil sample, and removing asphaltenes from the crude oil sample. The method further comprises determining an optical spectrum of maltenes of the crude oil sample, subtracting the optical spectrum of the maltenes of the crude oil sample from the optical spectrum of the crude oil sample to yield an optical spectrum of asphaltenes of the crude oil sample, and comparing the optical spectrum of the asphaltenes of the crude oil sample to predetermined calibration data.

In another aspect, the present invention provides a method for determining the asphaltene content of crude oil. The method comprises determining an optical spectrum of a first sample of the crude oil, removing asphaltenes from a second sample of the crude oil, and determining an optical spectrum of maltenes of the second sample of the crude oil. The method further comprises subtracting the optical spectrum of the maltenes of the second sample of the crude oil from the optical spectrum of the first sample of the crude oil to yield an optical spectrum of asphaltenes of the crude oil and comparing the optical spectrum of the asphaltenes of the crude oil to predetermined calibration data.

The present invention provides significant advantages, including (1) providing a method for determining asphaltene content of crude oil that is repeatable and reproducible; (2) providing a system and a method for determining asphaltene content of crude oil that are suitable for use at a wellsite; (3) providing a system and a method for determining asphaltene content of crude oil that are suitable for use on offshore platforms; (4) providing a system and a method for quickly determining asphaltene content of crude oil; (5) providing a system and a method for determining asphaltene content of crude oil that utilizes small sample volumes; (6) providing a system and a method for determining asphaltene content of crude oil that are not significantly affected by humidity; and (7) providing a system and a method for determining asphaltene content of crude oil that do not rely upon highly skilled operators.

Additional objectives, features, and advantages will be apparent in the written description which follows.

BRIEF DESCRIPTION OF THE DRAWINGS

The novel features of the invention are set forth in the appended claims. However, the invention itself, as well as a preferred mode of use, and further objectives and advantages thereof, will best be understood by reference to the following detailed description when read in conjunction with the accompanying drawings, in which the leftmost significant digit(s) in the reference numerals denote(s) the first figure in which the respective reference numerals appear, wherein:

Figure 1:
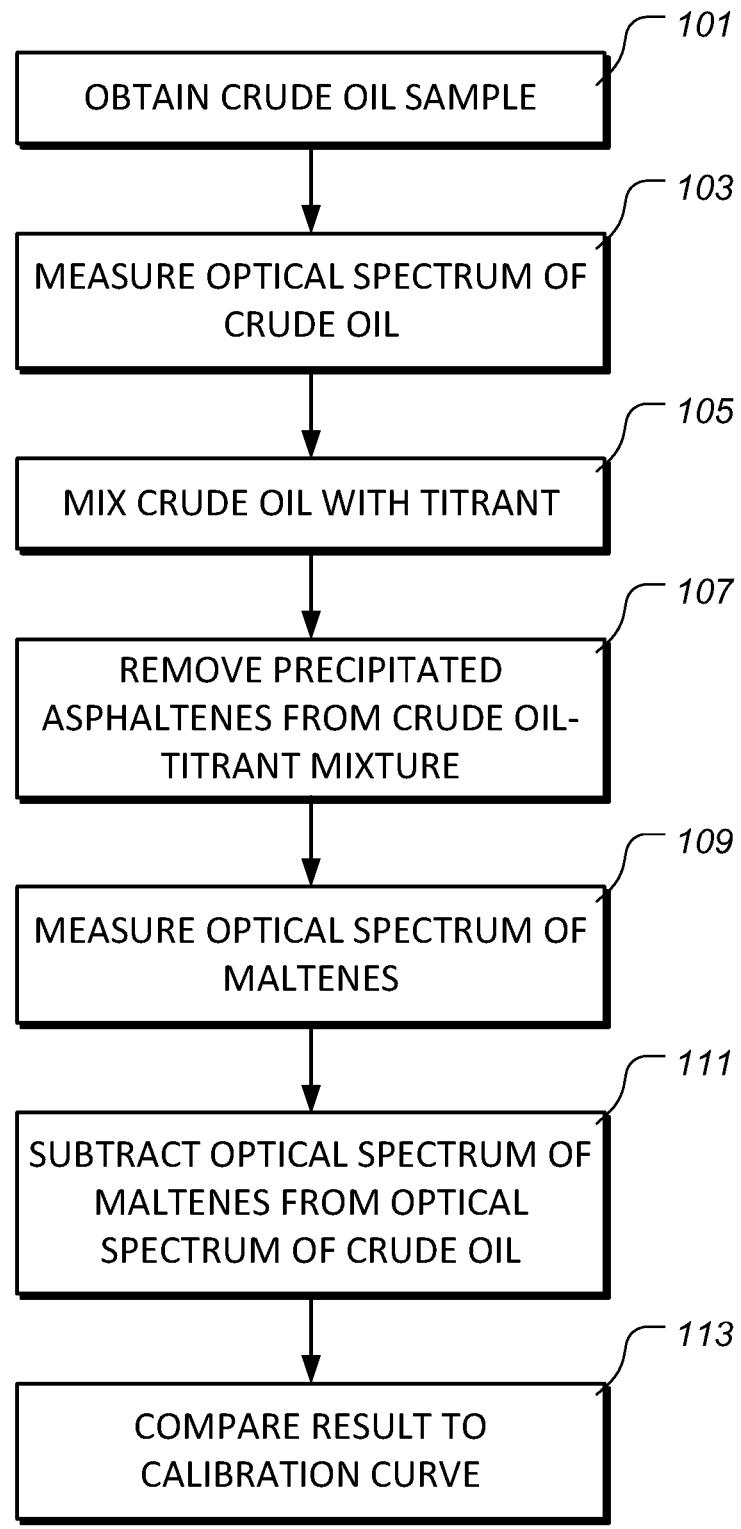
FIG. 1 is a flow chart representing an illustrative embodiment of a method for determining the asphaltene content of crude oil.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the scope of the invention as defined by the appended claims.

DETAILED DESCRIPTION OF THE INVENTION

Illustrative embodiments of the invention are described below. In the interest of clarity, not all features of an actual implementation are described in this specification. It will, of course, be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention relates to a system and method for determining the asphaltene content of crude oil. Generally, crude oil is made up of asphaltenes, which are insoluble in pentane or heptane, and maltenes, which are soluble in pentane and heptane. The asphaltene content of a sample of crude oil is determined by determining the optical spectrum of the asphaltenes in the crude oil and comparing the optical spectrum to predetermined calibration data, which provides a correlation between asphaltene optical spectra and asphaltene content. The asphaltene optical spectrum of the crude oil sample is determined by subtracting the optical spectrum of the maltenes of the crude oil sample from the optical spectrum of the crude oil sample.

FIG. 1 provides a flow chart representing an illustrative embodiment of a method for determining the asphaltene content of crude oil. In the illustrated embodiment, a crude oil sample is obtained (block 101). It should be noted that the obtained sample may be a sample that is retrieved and transported to another location, such as a laboratory, for analysis, or a sample that is retrieved and analyzed in the field, as is discussed in greater detail herein. The system and method of the present invention are also capable of being installed and used in a downhole tool. The scope of the present invention is not limited by the means by which the crude oil sample is obtained. Returning to FIG. 1, the optical spectrum of the crude oil sample is measured (block 103). The crude oil is then mixed with a titrant (block 105) to precipitate the asphaltenes from the crude oil. In one embodiment, the titrant is n-heptane, mixed at a ratio of one part crude oil to 40 parts n-heptane. However, other titrants, such as n-pentane or the like, and other mixing ratios are contemplated by the present invention. The precipitated asphaltenes are then removed from the crude oil-titrant mixture (block 107). The portion of the crude oil remaining after the precipitated asphaltenes are removed comprises maltenes, which are species having lower molecular weights than asphaltenes and are soluble in the titrant. The optical spectrum of the maltenes is measured (block 109), which is then subtracted from the optical spectrum of the crude oil prior to the asphaltenes being removed (block 111). The resulting optical spectrum corresponds to the optical spectrum of the asphaltenes in the sample of crude oil.

Figure 2:
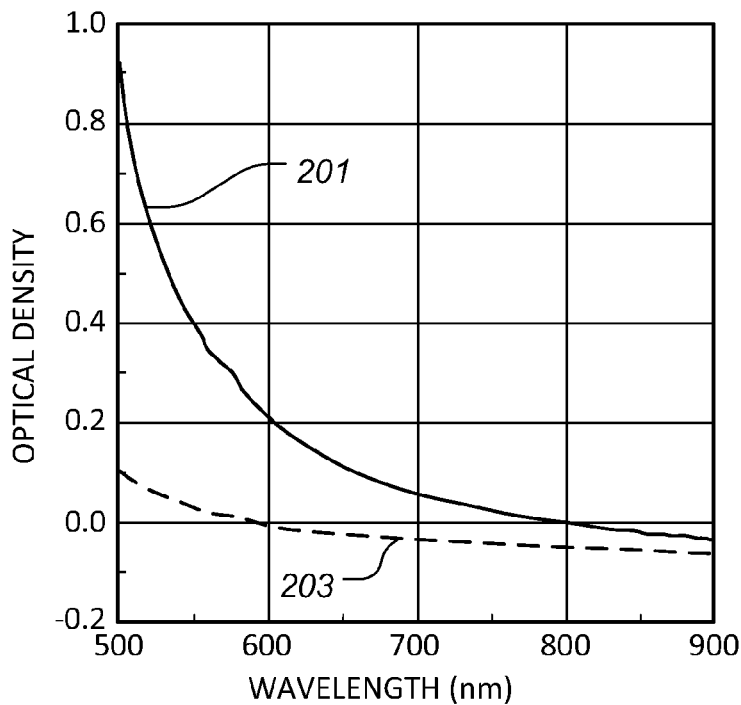
FIG. 2 is a graphical representation of an exemplary optical spectrum of a crude oil.

FIG. 2 depicts a graphical representation of an exemplary optical spectrum of a crude oil, represented by line 201, and of the maltenes in the crude oil, represented by line 203. The difference between these optical spectra is due to the optical spectrum of the asphaltenes in the crude oil. In one embodiment, the optical spectrum at one or more longer wavelengths of the maltenes of the crude oil sample, such as at wavelengths of about 800 nanometers, is subtracted from the optical spectrum at one or more shorter wavelengths of the maltenes of the crude oil sample, such as at wavelengths of about 600 nanometers, to reduce the error from a spectral offset introduced by light scattering and the effect of variation of refractive index in the measuring instrument. Returning to FIG. 1, the optical spectrum of the asphaltenes, i.e., the result from block 111, wherein the optical spectrum of maltenes of the crude oil is subtracted from the optical spectrum of the crude oil prior to the asphaltenes being removed, is compared to calibration data (block 113), such as a calibration curve. The calibration data correlates the optical spectrum of the asphaltene molecules to the asphaltene content measured using another technique, such as a conventional gravimetry technique, in which a series of crude oil samples are collected and tested.

Figure 3:
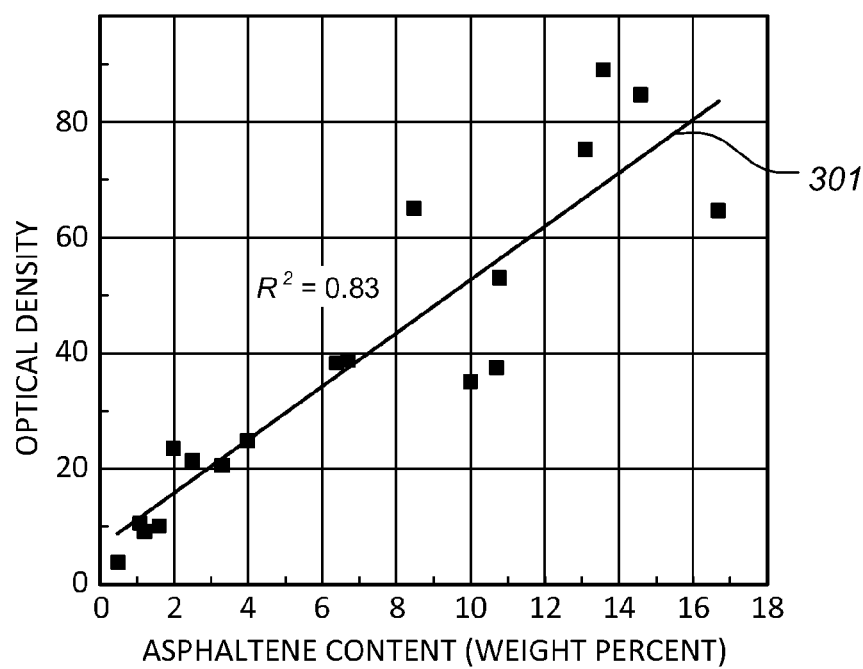
FIG. 3 is a graphical representation of one example of optical density of various samples of crude oil and their asphaltene contents.
Figure 4:
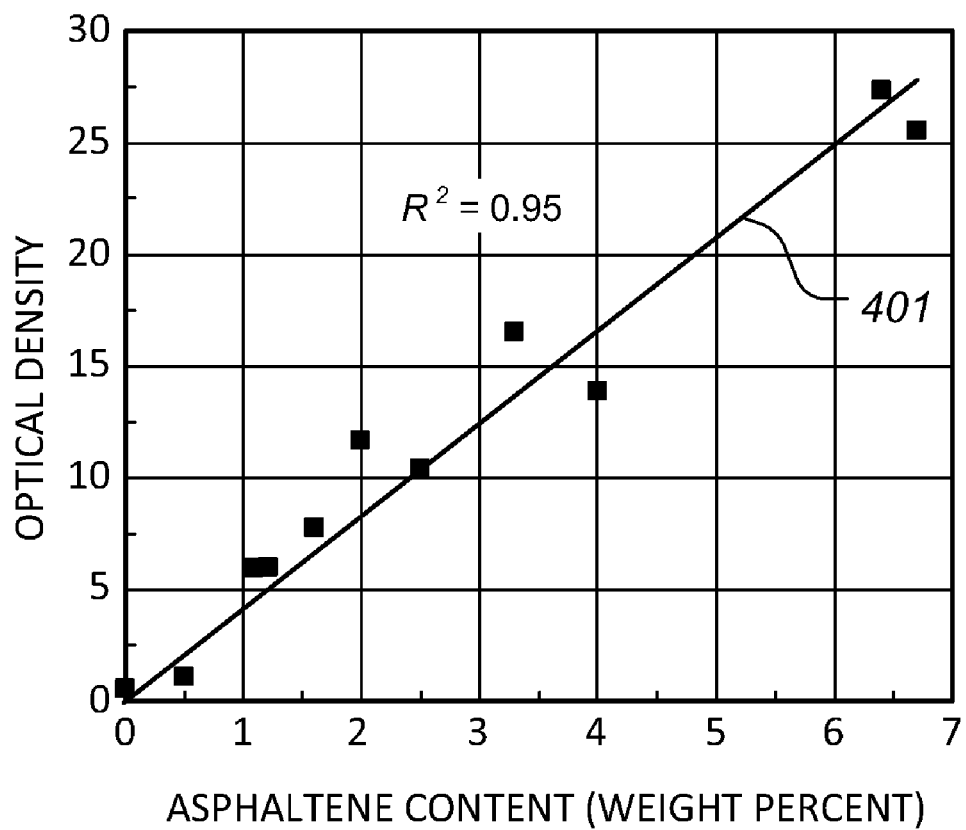
FIG. 4 is a graphical representation of an example of optical density of various samples of crude oil in which the optical spectra of the maltenes of the crude oil samples have been subtracted from the optical spectra of the crude oil samples.

FIGS. 3 and 4 illustrate the improvement in correlation between asphaltene optical density and asphaltene content when the optical spectrum of the maltenes in the crude oil is subtracted. FIG. 3 depicts a graphical representation of one example of the optical density of various samples of crude oil and their asphaltene contents. Line 301 represents a linear model generated using the optical density at a particular wavelength and the asphaltene contents of the samples. In this example, the linear model exhibits a coefficient of determination ($R^2$) of 0.83. Note that models exhibiting coefficients of determination that approach 1.00 fit the data well, while models having coefficients of determination that are less than 1.00 do not represent the data as well. FIG. 4 depicts a graphical representation of an example of the optical density of various samples of crude oil in which the optical density of the maltenes of the crude oil samples have been subtracted from the optical density of the crude oil samples. Line 401 represents a linear model generated using the resulting optical density and asphaltene contents of the samples. In the example of FIG. 4, the linear model exhibits a coefficient of determination of 0.95. Thus, the correlation between asphaltene content and the optical density of FIG. 4, i.e., the optical density of samples in which contributions by maltenes have been removed, is significantly better than the correlation between asphaltene content and the optical density of FIG. 3, i.e., the optical density of the base crude oil samples.

Figure 5:
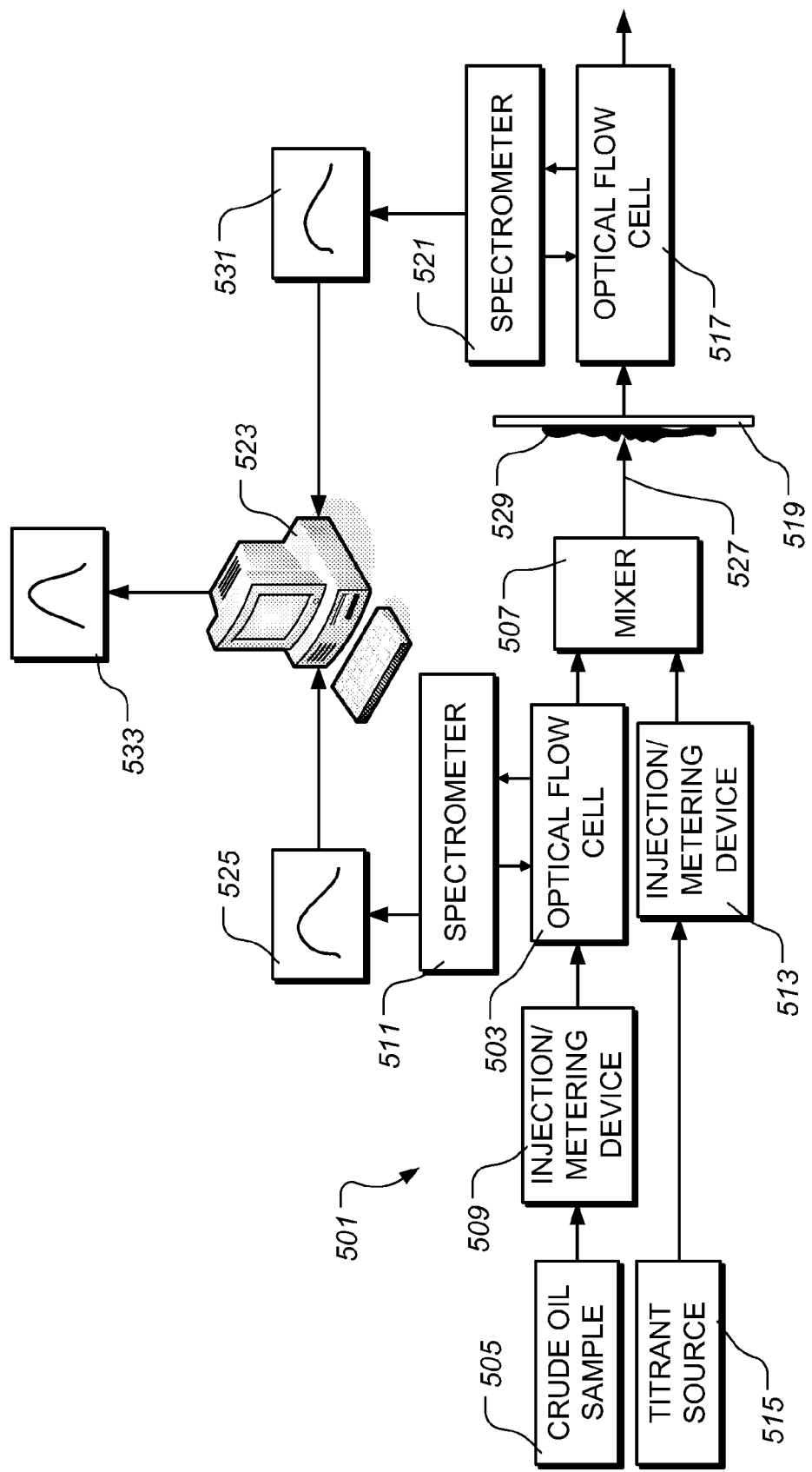
FIG. 5 is a stylized, graphical representation of a first illustrative embodiment of a system for determining the asphaltene content of crude oil.

FIG. 5 depicts a stylized, graphical representation of a first illustrative embodiment of a system 501 for determining the asphaltene content of crude oil. Specifically, in reference to FIG. 1, system 501 is configured to accomplish measuring an optical spectrum of a sample of crude oil (block 103), mixing the crude oil sample with a titrant (block 105), removing precipitated asphaltenes from the crude oil-titrant mixture (block 107), and measuring an optical spectrum of the maltenes of the crude oil sample (block 109). In the illustrated embodiment, system 501 comprises a first optical flow cell 503 that is in fluid communication with a crude oil sample 505 via a crude oil injection/metering device 509 and is in fluid communication with a mixer 507. In one embodiment, mixer 507 is a microfluidic mixer, such as those available from The Dolomite Centre Limited of Royston, UK. A first spectrometer 511 is operably associated with the first optical flow cell 503. A titrant injection/metering device 513 is in fluid communication with a titrant source 515 and mixer 507. In the illustrated embodiment, crude oil injection/metering device 509 and titrant injection/metering device 513 are pumps, such as syringe pumps available from Thermo Fisher Scientific Inc. of Pittsburgh, Pa., USA. Mixer 507 is in fluid communication with a second optical flow cell 517 via a filtration unit 519. In the illustrated embodiment, optical flow cells 503 and 517 are optical flow cells such as those available from Ocean Optics, Inc. of Dunedin, Fla., USA. Filtration unit 519, in the illustrated embodiment, is a microfluidic membrane filtration unit, such as those available from The Dolomite Centre Limited. A second spectrometer 521 is operably associated with second optical flow cell 517. In the illustrated embodiment, spectrometers 511 and 521 are spectrometers such as those available from Ocean Optics, Inc. First spectrometer 511 and second spectrometer 521 are operably associated, in the illustrated embodiment, with a comparator 523, such as a computer, although certain embodiments of system 501 omit comparator 523, wherein the functions of comparator 523 are performed by human or other means.

Still referring to FIG. 5, an exemplary operation of system 501 for determining the asphaltene content of crude oil is disclosed. At least a portion of crude oil sample 505 is transmitted to first optical flow cell 503 by crude oil injection/metering device 509. First spectrometer 511 analyzes the portion of crude oil sample 505 disposed in first optical flow cell 503 and determines an optical spectrum of the portion of crude oil sample 505, represented by graph 525. The crude oil from crude oil sample 505 is further urged to mixer 507 by crude oil injection/metering device 509. A titrant, such as heptane, pentane, or the like, is transmitted from titrant source 515 to mixer 507 by titrant injection/metering device 513. Crude oil and the titrant are mixed in mixer 507 at a predetermined ratio, such as at a ratio of about one part crude oil to about 40 parts titrant. Once the crude oil and titrant are mixed, the titrant causes the asphaltenes in the crude oil to be precipitated in a channel, represented by arrow 527. The crude oil-titrant mixture is then filtered by filtration unit 519, which retains precipitated asphaltenes 529 and allows the remaining fluid, i.e., the maltenes of the sample of crude oil, to pass therethrough to second optical flow cell 517. Second spectrometer 521 analyzes the maltenes in second optical flow cell 517 and determines an optical spectrum of the maltenes, represented by graph 531. The optical spectrum of the crude oil, i.e., represented by graph 525, and the optical spectrum of the maltenes of the crude oil, i.e., represented by graph 531, are fed to comparator 523, where the optical spectrum of the maltenes of the crude oil is subtracted from the optical spectrum of the crude oil, resulting in the optical spectrum of the asphaltenes in the crude oil, represented by graph 533. The optical spectrum of the asphaltenes in the crude oil is then compared to predetermined calibration data, such as a predetermined calibration curve, as discussed herein, to measure the asphaltene content of crude oil sample 505.

Figure 6A:
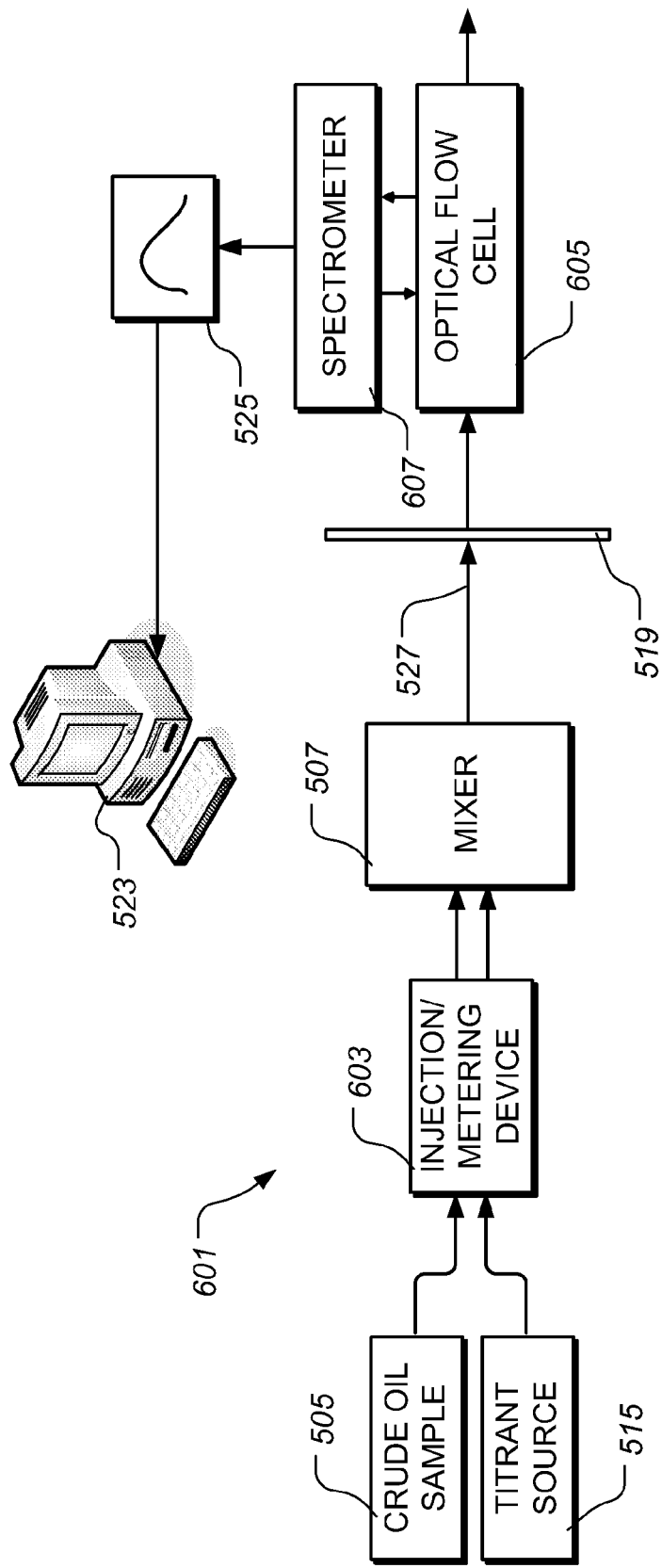
FIGS. 6A and 6B are stylized, graphical representations of a second illustrative embodiment of a system for determining the asphaltene content of crude oil.
Figure 6B:
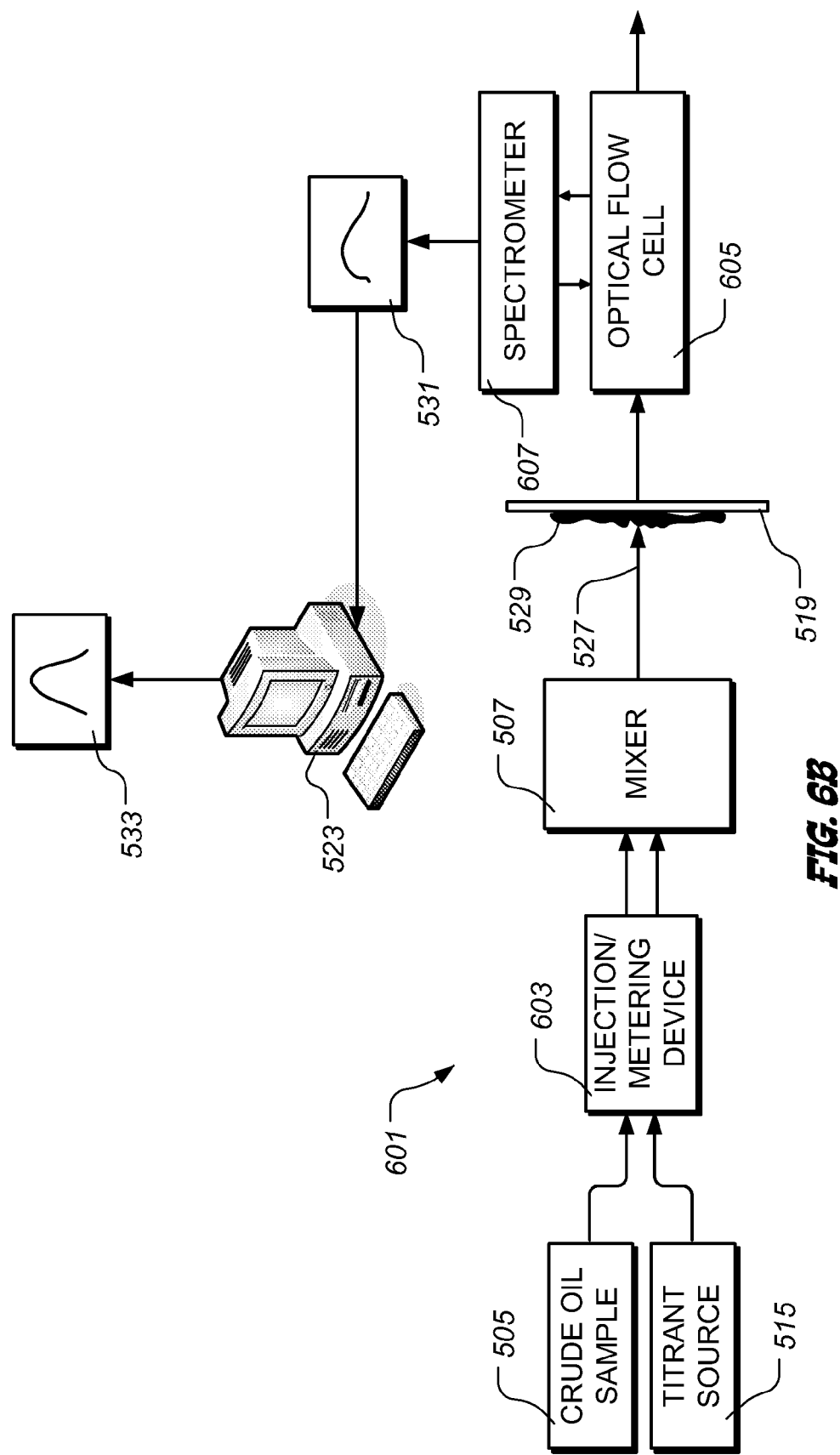

FIGS. 6A and 6B depict a stylized, graphical representation of a second illustrative embodiment of a system 601 for determining the asphaltene content of crude oil. In this embodiment, injection/metering devices 509 and 513 of system 501 are replaced with an injection/metering device 603, optical flow cells 503 and 517 of system 501 are replaced with an optical flow cell 605, and spectrometers 511 and 521 of system 501 are replaced with a spectrometer 607. In one embodiment, injection/metering device 603 corresponds to one of injection/metering devices 509 and 513 of system 501, optical flow cell 605 corresponds to one of optical flow cells 503 and 517 of system 501, and spectrometer 607 corresponds to one of spectrometers 511 and 521 of system 501. Otherwise, the elements of system 601 correspond to those of system 501. As in the embodiment of FIG. 5, the embodiment of FIGS. 6A and 6B is configured to accomplish measuring an optical spectrum of a sample of crude oil (block 103), mixing the crude oil sample with a titrant (block 105), removing precipitated asphaltenes from the crude oil-titrant mixture (block 107), and measuring an optical spectrum of the maltenes of the crude oil sample (block 109), shown in FIG. 1.

In the embodiment illustrated in FIGS. 6A and 6B, mixer 507 is in fluid communication with crude oil sample 505 and titrant source 515 via injection/metering device 603. Mixer 507 is in fluid communication with optical flow cell 605 via filtration unit 519. Spectrometer 607 is operably associated with optical flow cell 605. In the illustrated embodiment, spectrometer 607 is operably associated with comparator 523, although certain embodiments of system 601 omit comparator 523, wherein the functions of comparator 523 are performed by human or other means.

Still referring to FIGS. 6A and 6B, an exemplary operation of system 601 for determining the asphaltene content of crude oil is disclosed. In FIG. 6A, a first portion of crude oil sample 505 is transmitted through mixer 507 and filtration unit 519 to optical flow cell 605 by injection/metering device 603. Spectrometer 607 analyzes the crude oil disposed in optical flow cell 605 and determines an optical spectrum of the crude oil, represented by graph 525. In the illustrated embodiment, the optical spectrum of the crude oil, i.e., represented by graph 525, is fed to comparator 523 for use in determining the asphaltene content of crude oil sample 505. The flow path of crude oil in system 601 is then cleaned.

Referring to FIG. 6B, a second portion of crude oil sample 505 and a titrant, such as heptane, pentane, or the like, is transmitted to mixer 507 by injection/metering device 603. The second portion of crude oil sample 505 and the titrant are mixed in mixer 507 at a predetermined ratio, such as at a ratio of about one part crude oil to about 40 parts titrant. Once the second portion of crude oil sample 505 and the titrant are mixed, the titrant causes the asphaltenes in the crude oil to precipitate in the channel represented by arrow 527. The crude oil-titrant mixture is then filtered by filtration unit 519, which retains precipitated asphaltenes 529 and allows the remaining fluid, i.e., the maltenes of the sample of crude oil, to pass therethrough to optical flow cell 605. Spectrometer 607 analyzes the maltenes in optical flow cell 605 and determines an optical spectrum of the maltenes, represented by graph 531. In the illustrated embodiment, the optical spectrum of the maltenes of the crude oil, i.e., represented by graph 531, is fed to comparator 523, where the optical spectrum of the maltenes of the crude oil is subtracted from the optical spectrum of the crude oil, resulting in the optical spectrum of the asphaltenes in the crude oil, represented by graph 533. The optical spectrum of the asphaltenes in the crude oil is then compared to predetermined calibration data, such as a predetermined calibration curve, as discussed herein, to measure the asphaltene content of the crude oil. As discussed herein concerning the embodiment of FIG. 5, certain embodiments of system 601 omit comparator 523, wherein the functions of comparator 523 are performed by human or other means.

It should be noted that, in certain embodiments, the modifications made to system 501 (shown in FIG. 5) resulting in system 601 may be incorporated singly or in any combination. For example, system 601 may be modified such that injection/metering devices 509 and 513 of system 501 are replaced with injection/metering device 603, but optical flow cells 503 and 517 and spectrometers 511 and 521 are not replaced. In another example, system 601 may be modified such that optical flow cells 503 and 517 of system 501 are replaced with optical flow cell 605 but injection/metering devices 509 and 513 and spectrometers 511 and 521 are not replaced. In yet another example, system 601 may be modified such that spectrometers 511 and 521 of system 501 are replaced with spectrometer 607 but injection/metering devices 509 and 513 and optical flow cells 503 and 517 are not replaced. The present invention further contemplates various combinations of these embodiments.

Figure 7:
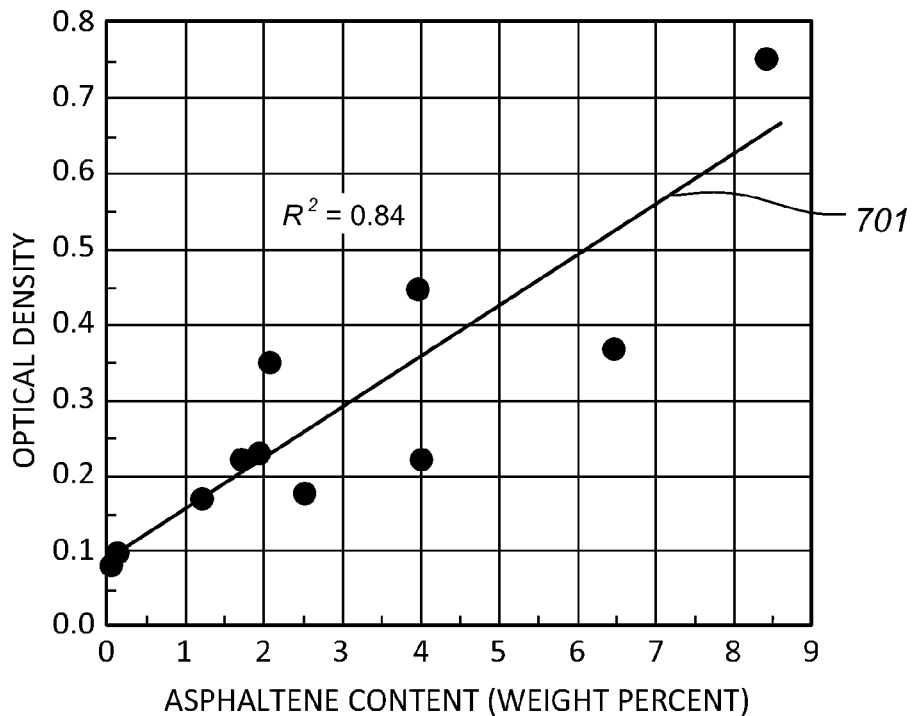
FIG. 7 is a graphical representation of one example of optical density of various samples of crude oil using either the system of FIG. 5 or the system of FIGS. 6A and 6B.
Figure 8:
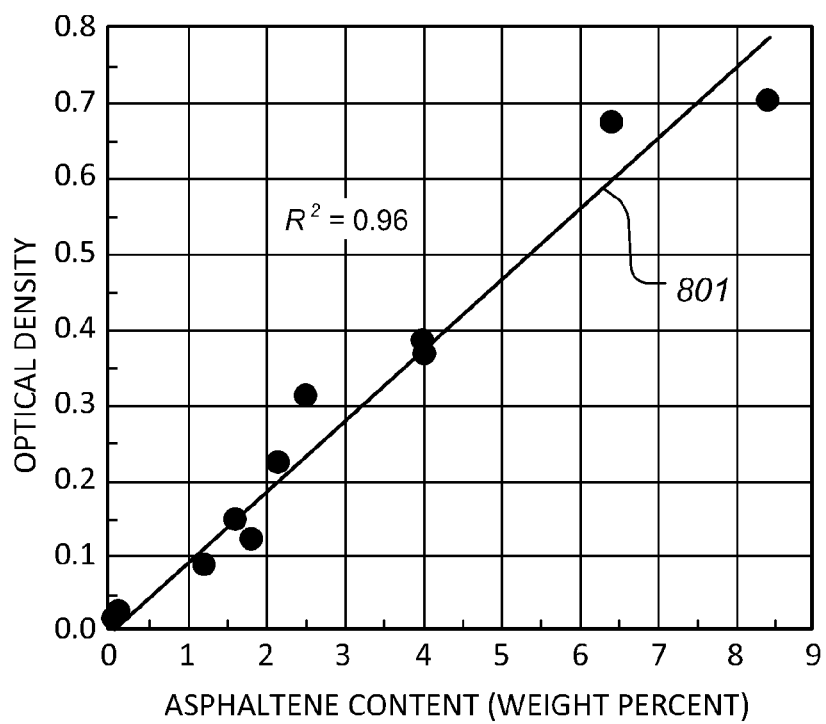
FIG. 8 is a graphical representation of an example of optical density of various samples of crude oil in which the optical spectra of the maltenes of the crude oil samples have been subtracted therefrom using either the system of FIG. 5 or the system of FIGS. 6A and 6B.

FIG. 7 depicts a graphical representation of one example of the optical density of various samples of crude oil, such as crude oil sample 505, as determined by first spectrometer 511 and their asphaltene contents. Line 701 represents a linear model generated using the optical density at a particular wavelength and asphaltene contents of the samples. In this example, the linear model exhibits a coefficient of determination ($R^2$) of 0.84, which is comparable to that shown in FIG. 3. FIG. 8 depicts a graphical representation of an example of optical density at a particular wavelength of asphaltenes of various samples of crude oil in which the optical spectra of the maltenes of the crude oil samples have been subtracted from the optical spectra of the crude oil samples. Line 801 represents a linear model generated using the resulting optical density and asphaltene contents of the samples. In the example of FIG. 8, the linear model exhibits a coefficient of determination of 0.96, which is comparable to that shown in FIG. 4. Thus the correlation between asphaltene content and the optical density of FIG. 8, i.e., the optical density of samples in which contributions by maltenes have been removed, is significantly better than the correlation between asphaltene content and the optical density of FIG. 7, i.e., the optical density of the base crude oil samples.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope of the invention. Accordingly, the protection sought herein is as set forth in the claims below. Although the present invention is shown in a limited number of forms, it is not limited to just these forms, but is amenable to various changes and modifications.

What is claimed is:

1. A system for determining the asphaltene content of crude oil, comprising:
   a first optical flow cell;
   a first spectrometer operably associated with the first optical flow cell;
   a mixer in fluid communication with the first optical flow cell;
   a crude oil injection/metering device configured to receive the crude oil, the crude oil injection/metering device being in fluid communication with the first optical flow cell;
   a titrant injection/metering device in fluid communication with the mixer, the titrant injection/metering device configured to receive a titrant;
   a filtration unit in fluid communication with the mixer;
   a second optical flow cell in fluid communication with the filtration unit; and
   a second spectrometer operably associated with the second optical flow cell.

2. The system of claim 1, wherein the mixer is a microfluidic mixer.

3. The system of claim 1, wherein at least one of the crude oil injection/metering device and the titrant injection/metering device is a syringe pump.

4. The system of claim 1, wherein the filtration unit is a microfluidic membrane filtration unit.

5. The system of claim 1, further comprising a comparator operably associated with the first spectrometer and the second spectrometer, the comparator being operable to yield an optical spectrum of asphaltenes in the crude oil.

6. The system of claim 1, wherein the system is installed in downhole tool.

7. A system for determining the asphaltene content of crude oil, comprising:
   an injection/metering device configured to receive the crude oil and a titrant;
   a mixer in fluid communication with the injection/metering device;
   a filtration unit in fluid communication with the mixer;
   an optical flow cell in fluid communication with the filtration unit; and
   a spectrometer operably associated with the optical flow cell.

8. The system of claim 7, wherein the mixer is a microfluidic mixer.

9. The system of claim 7, wherein the injection/metering device is a syringe pump.

10. The system of claim 7, wherein the filtration unit is a microfluidic membrane filtration unit.

11. The system of claim 7, further comprising a comparator operably associated with the spectrometer, the comparator being operable to yield an optical spectrum of asphaltenes in the crude oil.

12. The system of claim 7, wherein the system is installed in a downhole tool.

13. A method for determining the asphaltene content of crude oil, comprising:
   obtaining a crude oil sample;
   determining an optical spectrum of the crude oil sample;
   removing asphaltenes from the crude oil sample;
   determining an optical spectrum of maltenes of the crude oil sample;
   subtracting the optical spectrum of the maltenes of the crude oil sample from the optical spectrum of the crude oil sample to yield an optical spectrum of asphaltenes of the crude oil sample; and
   comparing the optical spectrum of the asphaltenes of the crude oil sample to predetermined calibration data.

14. The method of claim 13, wherein determining the optical spectrum of the crude oil sample is accomplished by analyzing at least a portion of the crude oil sample with a spectrometer.

15. The method of claim 14, wherein analyzing the at least a portion of the crude oil sample with the spectrometer is accomplished by disposing the at least a portion of the crude oil sample in an optical flow cell and analyzing the at least a portion of the crude oil sample disposed in the optical flow cell with the spectrometer.

16. The method of claim 13, wherein removing the asphaltenes from the crude oil sample is accomplished by mixing the crude oil sample with a titrant and removing precipitated asphaltenes from the crude oil-titrant mixture.

17. The method of claim 16, wherein mixing the crude oil sample with the titrant is accomplished by mixing the crude oil sample with the titrant in a microfluidic mixer.

18. The method of claim 16, wherein removing the precipitated asphaltenes from the crude oil-titrant mixture is accomplished using a microfluidic membrane filtration unit.

19. The method of claim 13, wherein subtracting the optical spectrum of the maltenes of the crude oil sample from the optical spectrum of the crude oil sample to yield the optical spectrum of the asphaltenes of the crude oil sample is accomplished using a comparator.

20. The method of claim 13, wherein determining the optical spectrum of the maltenes of the crude oil sample is accomplished by analyzing at least a portion of the de-asphaltenated crude oil sample with a spectrometer.

21. The method of claim 20, wherein analyzing the at least a portion of the de-asphaltenated crude oil sample with the spectrometer is accomplished by disposing the at least a portion of the de-asphaltenated crude oil sample in an optical flow cell and analyzing the at least a portion of the de-asphaltenated crude oil sample disposed in the optical flow cell with the spectrometer.

22. The method of claim 13, further comprising subtracting the optical spectrum at one or more longer wavelengths of the maltenes of the crude oil sample from the optical spectrum at one or more shorter wavelengths of the maltenes of the crude oil sample prior to subtracting the optical spectrum of the maltenes of the crude oil sample from the optical spectrum of the crude oil sample to yield the optical spectrum of the asphaltenes of the crude oil sample.

23. The method of claim 22, wherein subtracting the optical spectrum at one or more longer wavelengths of the maltenes of the crude oil sample from the optical spectrum at one or more shorter wavelengths of the maltenes of the crude oil sample is accomplished by subtracting the optical spectrum at a wavelength of about 800 nanometers of the maltenes of the crude oil sample from the optical spectrum at a wavelength of about 600 nanometers of the maltenes of the crude oil sample.

24. A method for determining the asphaltene content of crude oil, comprising:
  determining an optical spectrum of a first sample of the crude oil;
  removing asphaltenes from a second sample of the crude oil;
  determining an optical spectrum of maltenes of the second sample of the crude oil;
  subtracting the optical spectrum of the maltenes of the second sample of the crude oil from the optical spectrum of the first sample of the crude oil to yield an optical spectrum of asphaltenes of the crude oil; and
  comparing the optical spectrum of the asphaltenes of the crude oil to predetermined calibration data.

25. The method of claim 24, wherein determining the optical spectrum of the first sample of the crude oil is accomplished by analyzing at least a portion of the first sample of the crude oil with a spectrometer.

26. The method of claim 25, wherein analyzing the at least a portion of the first sample of the crude oil with the spectrometer is accomplished by disposing the at least a portion of the first sample of the crude oil in an optical flow cell and analyzing the at least a portion of the first sample of the crude oil disposed in the optical flow cell with the spectrometer.

27. The method of claim 24, wherein removing the asphaltenes from the second sample of the crude oil is accomplished by mixing the second sample of the crude oil with a titrant and removing precipitated asphaltenes from the crude oil-titrant mixture.

28. The method of claim 27, wherein mixing the second sample of the crude oil with the titrant is accomplished in a microfluidic mixer.

29. The method of claim 27, wherein removing the precipitated asphaltenes from the crude oil-titrant mixture is accomplished using a microfluidic membrane filtration unit.

30. The method of claim 24, wherein subtracting the optical spectrum of the maltenes of the second sample of the crude oil from the optical spectrum of the first sample of the crude oil to yield an optical spectrum of asphaltenes of the crude oil is accomplished using a comparator.

31. The method of claim 24, wherein determining the optical spectrum of the maltenes of the second sample of the crude oil is accomplished by analyzing at least a portion of the de-asphaltenated second sample of the crude oil with a spectrometer.

32. The method of claim 31, wherein analyzing at least a portion of the second sample of the crude oil with the spectrometer is accomplished by disposing the at least a portion of the de-asphaltenated second sample of the crude oil in an optical flow cell and analyzing the at least a portion of the de-asphaltenated second sample of the crude oil disposed in the optical flow cell with the spectrometer.

33. The method of claim 24, further comprising subtracting the optical spectrum at one or more longer wavelengths of the maltenes of the second sample of the crude oil from the optical spectrum at one or more shorter wavelengths of the maltenes of the second sample of the crude oil prior to subtracting the optical spectrum of the maltenes of the second sample of the crude oil from the optical spectrum of the first sample of the crude oil to yield the optical spectrum of the asphaltenes of the crude oil.

34. The method of claim 33, wherein subtracting the optical spectrum at one or more longer wavelengths of the maltenes of the second sample of the crude oil from the optical spectrum at one or more shorter wavelengths of the maltenes of the second sample of the crude oil is accomplished by subtracting the optical spectrum at a wavelength of about 800 nanometers of the maltenes of the second sample of the crude oil from the optical spectrum at a wavelength of about 600 nanometers of the maltenes of the second sample of the crude oil.

* * * * *